United States Patent [19]

Kim et al.

[11] 4,401,832
[45] Aug. 30, 1983

[54] PROCESS FOR PREPARING α-[(ALKYLAMINO)METHYL]-β-ARYLOXY-BENZENEETHANOLS

[75] Inventors: Dong H. Kim, Wayne; Stanley C. Bell, Penn Valley, both of Pa.

[73] Assignee: American Home Products Corporation, New York, N.Y.

[21] Appl. No.: 291,896

[22] Filed: Aug. 10, 1981

Related U.S. Application Data

[62] Division of Ser. No. 921,294, Jul. 3, 1978, Pat. No. 4,341,718.

[51] Int. Cl.³ .......................................... C07C 83/00
[52] U.S. Cl. ............................. 564/347; 260/501.18; 424/316; 424/330; 564/142; 564/161; 564/170; 564/172; 564/175; 564/349; 549/525; 549/548
[58] Field of Search ................ 564/347, 348; 549/525, 549/548

[56] References Cited

U.S. PATENT DOCUMENTS

| | | | |
|---|---|---|---|
| 2,336,093 | 12/1944 | Grun et al. | 564/348 X |
| 2,695,919 | 11/1954 | Wright et al. | 564/348 |
| 2,920,079 | 1/1960 | Hudson | 549/548 X |
| 3,106,564 | 10/1963 | Fleming et al. | 564/347 X |

OTHER PUBLICATIONS

Pedersen, C. J., "Cyclic Polyethers and their Complexes with Metal Salts", J. Am. Chem. Soc., 89, 7017–7036 (1967).
Knipe, A. C., "Crown Ethers", J. Chem. Ed., 53, 618–622 (1976).
Fieser, M. & Fieser, L. F., Reagent for Organic Synthesis, vol. 5, pp. 152–155 (John Wiley & Son, N.Y. 1975).
Thomassen, L. M., "The Effect of the Solvent on the Reactivity of Potassium Phenoxide in Nucleophilic Substitution Reactions, Part IV, Cyclic Polyethers as Additives", Acta. Chem. Scand., 25, 3024–3030 (1971).

*Primary Examiner*—Robert V. Hines
*Attorney, Agent, or Firm*—Arthur G. Seifert

[57] ABSTRACT

Disclosed herein are α-[(alkylamino)methyl]-β-aryloxy-benzeneethanols exhibiting antiarrhythmic activity and having the following formula:

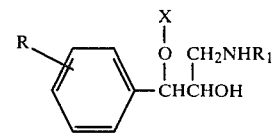

wherein R is hydrogen, halogen, lower alkyl, or lower alkoxy; X is phenyl, 1-naphthyl, or a phenyl group substituted by a halogen, a lower alkyl group, or a lower alkoxy group; $R_1$ is lower alkyl; and pharmacologically acceptable acid addition salts thereof. Also disclosed is a process for the addition of an aryloxy group at the 3-position of a 3-phenyl-2-oxiranecarboxamide to produce an α-hydroxy-β-aryloxy-benzenepropanamide, said process comprising contacting an alkali metal aryloxide with said 3-phenyl-2-oxiranecarboxamide in the presence of a crown ether. Such α-hydroxy-β-aryloxy-benzenepropanamides may then be reduced to produce the compounds of the invention.

5 Claims, No Drawings

PROCESS FOR PREPARING α-[(ALKYLAMINO)METHYL]-β-ARYLOXY-BENZENEETHANOLS

This is a division of application Ser. No. 921,294 filed July 3, 1978 and now U.S. Pat. No. 4,341,718.

BACKGROUND OF THE INVENTION

This invention comprises α-[(alkylamino)methyl]-β-aryloxy-benzeneethanols and the pharmacologically acceptable acid addition salts thereof, which in standard pharmacological tests with animals have exhibited antiarrhythmic activity.

Heretofore an α-[(alkylamino)methyl]ethanol substituted in the β-position by both a phenyl group and a phenoxy (or 1-naphthoxy) group has not been known. Recently, α-[(1-methylethylamino)methyl]-γ-phenyl-(γ-benzene)propanol was reported to have antiarrhythmic activity by Murphy et al. in The Pharmacologist, 18, 114 (1976). An earlier Derwent abstract No. 16,563, of French Pat. No. 1,394,771, published Sept. 4, 1965, disclosed certain alkanolamine derivatives to be β-adrenergic blockers. Among these was α-[(1-methylethylamino)methyl]-3-alkyl-(2-iodo)benzeneethanol.

A further aspect of the present invention is a process for the addition of an aryloxy group at the 3-position of a 3-phenyl-2-oxiranecarboxamide to produce an α-hydroxy-β-aryloxybenzenepropanamide, said process comprising contacting an alkali metal aryloxide with said 3-phenyl-2-oxiranecarboxamide in the presence of a crown ether. The preparation and use of "crown ethers" as metal ion complexing agents is reported in Fieser and Fieser, *Reagents for Organic Synthesis*, Vol. V, pp. 152–5, Wiley-Interscience (1975) and Knipe, J. Chem. Ed., 53, 618 (1976). The influence of dibenzo or dicyclohexyl-[3n]-crown[n] crown ethers on the reaction of potassium phenoxide and butyl bromide to form phenylbutyl ether is reported on by Thomassen et al., in J. Acta Chem. Scand, 25, 3024 (1971).

SUMMARY OF THE INVENTION

The compounds of the present invention are represented by the formula I:

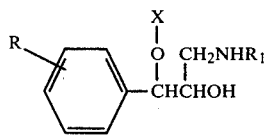

wherein R is hydrogen, halogen, lower alkyl, or lower alkoxy; X is phenyl, 1-naphthyl, or a phenyl group substituted by a halogen, a lower alkyl group, or a lower alkoxy group; and $R_1$ is a lower alkyl group.

A preferred group (A) of compounds of formula I are those in which the R substituent is in the 3-position on the phenyl ring.

A particularly preferred group (B) of compounds of formula I are those in which R is hydrogen, 3-chloro or 3-methoxy and X is phenyl, 1-naphthyl, or phenyl substituted by chlorine, a methyl group, or a methoxy group.

A most preferred group (C) of compounds of formula I are those in which R is hydrogen and X is phenyl, 1-naphthyl, or phenyl substituted by chlorine, a methyl group, or a methoxy group.

Also, particularly preferred is the compound (D) in which R is hydrogen and X is 1-naphthyl.

Particularly preferred are those compounds of formula I in which $R_1$ is a 1-methylethyl (i.e. isopropyl) group.

Another group of most preferred compounds (E) are those in which R is 3-chloro or 3-methoxy, and X is phenyl.

Included in the present invention are the pharmacologically acceptable acid addition salts of the compounds of formula I. The nitric acid, hydrochloric acid, and oxalic acid salts are particularly preferred salts.

With respect to the compounds of group C described above, the nitric acid and hydrochloric acid addition salts are particularly preferred salts. With respect to the compound D described above, the nitric acid salts are particularly preferred salts. With respect to the compounds of group E described above, the nitric acid and oxalic acid salts are particularly preferred salts.

A further aspect of the Applicants' invention is a process for the addition of an aryloxy group at the 3-position of a 3-phenyl-2-oxiranecarboxamide to produce an α-hydroxy-β-aryloxybenzenepropanamide, said process comprising contacting an alkali metal aryloxide with said 3-phenyl-2-oxiranecarboxamide in the presence of a crown ether. Said α-hydroxy-β-aryloxybenzenepropanamide may then be reduced to produce a compound of the invention.

In this addition reaction, the preferred alkali metals are sodium and potassium, with sodium being most preferred, and the preferred crown ethers are non-aromatic 18-crown-6-ethers, with 18-crown-6 being most preferred.

As used herein, the term "aryloxy" means phenoxy, 1-naphthoxy, or phenoxy wherein the phenyl ring thereof is substituted with halogen, a lower alkyl group, or a lower alkoxy group. The term "lower alkyl" means an aliphatic hydrocarbon group containing 1–4 carbon atoms, e.g. methyl, ethyl, propyl, isopropyl, butyl, isobutyl, s-butyl, or t-butyl groups. The methyl group is especially preferred. The term "lower alkoxy" means an aliphatic oxy group having 1–4 carbon atoms, e.g. methoxy, ethoxy, propoxy, isopropoxy, butoxy, isobutoxy, s-butoxy, or t-butoxy groups. The methoxy group is especially preferred.

Further, as used herein, a reference to "a 3-phenol-2-oxiranecarboxamide" refers to a compound having the structural formula as shown for intermediate V of the flow diagram illustrated in the following section wherein the carbon atom of the carboxyl group is designated number 1, the amide group is substituted with an $R_1$ substituent, and the 3-phenyl group thereof may be substituted with R substituents as defined in reference to Formula I. Thus, the illustrative compound shown as intermediate V is named N-(1-methylethyl)-3-phenyl-2-oxiranecarboxamide. Referring still to the flow diagram, the precursors of said 3-phenyl-2-oxiranecarboxamides, namely the "N-(lower alkyl)cinnamoylcarboxamides (IV)", the "cinnamoylchlorides (III)", and the "cinnamic acids (II)" also may be substituted on the phenyl ring thereof with an R substituent as defined in reference to Formula I.

As used herein, a reference to "an α-hydroxy-β-aryloxybenzenepropanamide" refers to a compound having the structural formula for intermediate VI or VII of flow diagram wherein the carbon atom to which the hydroxyl group is attached is designated "α" and the amide group contains a lower alkyl substituent. The benzene ring thereof corresponds to the 3-phenyl ring of its precursor 3-phenyl-2-oxiranecarboxamide (V) and may be similarly substituted with an R substituent as defined in reference to Formula I. "Aryloxy" was defined above, and the aryl substituent of said β-aryloxy group is defined the same as the X substituent of Formula I. For example, the illustrative compound shown in the flow diagram as intermediate VI is named α-hydroxy-β-phenoxy-N-(1-methylethyl)benzene-propanamide.

DETAILED DESCRIPTION OF THE INVENTION

The general method of synthesis of the compounds of Formula I is illustrated in the flow diagram below which depicts the preparation of a specific embodiment of the invention for purposes of illustration, namely α-[(1-methylethylamino)methyl]-β-phenoxy-benzeneethanol:

ferred, those skilled in the art of chemistry will understand that other reagents, such as phosphorus trichloride and phosphorus pentachloride, may be used under known reaction conditions in order to form the cinnamoyl chloride desired. Similarly, it is preferred to form the cinnamoyl chloride, but other halides may be formed to serve the same function, as known to those skilled in the art.

B. Isopropylamine is then reacted with the resulting cinnamoyl chloride (III) in order to form N-(1-methylethyl)cinnamoylcarboxide (IV). This reaction is carried out in an inert organic solvent, such as benzene, for example first at room temperature and then under reflux heating to produce the N-(1-methylethyl)cinnamoylcarboxamide (IV). If it is desired to form a compound of the invention with an $R_1$ substituent other than the 1-methylethyl (i.e. isopropyl) group, then the appropriate lower alkylamine should be used instead of isopropylamine in this reaction.

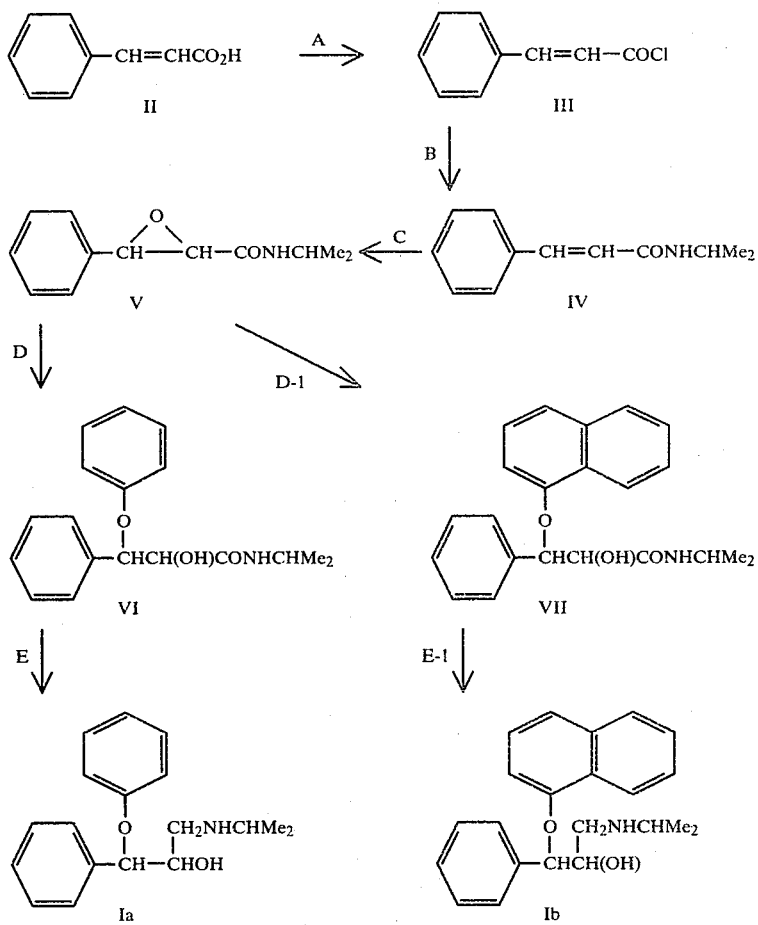

FIG. 1

Using flow diagram in which the compounds are given Roman numerals for identification and each step in the production of the compounds of the invention is given a capital letter designation, the description of the production of the compounds of the invention is as follows:

A. Cinnamic acid (II) is reacted with thionyl chloride to produce cinnamoyl chloride (III). The reaction is carried out in an inert organic solvent, such as benzene, at reflux. Although the use of thionyl chloride is pre- C. The N-(1-methylethyl)-3-phenyl-2-oxiranecarboxamide (V) intermediate is formed by the epoxidation of the alkene bond of the N-(1-methylethyl)cinnamoylcarboxamide (IV) using an epoxidizing agent, such as m-chloroperbenzoic acid, in the presence of a radical inhibitor. This reaction is conveniently carried out according to the method of Kishi et al. in J.C.S. Chem. Comm., 64 (1972) using the preferred radical inhibitor 4,4'-thiobis-(6-t-butyl-3-methyl-phenol). The reaction is preferably performed using ethylene dichloride as an inert solvent and on the other of 1 percent by weight of the preferred radical inhibitor 4,4'-thiobis-(6-t-butyl-3-methyl-phenol) relative to m-chloroperbenzoic acid under gentle reflux for approximately 1 hour.

D. The addition of the phenoxy group to the 3-position of N-(1-methylethyl)-3-phenyl-2-oxiranecarboxamide (V) intermediate to form α-hydroxy-β-phenoxy-N-(1-methylethyl)benzenepropanamide (VI) is carried out in an inert organic solvent, acetonitrile being preferred, in the presence of a crown ether, such as 18-crown-6.

In order to prepare the sodium phenoxide reactant, phenol may be converted to its sodium salt by first dissolving the phenol in a freshly prepared sodium methoxide-methanol solution and subsequently evaporating the excess methanol. The resulting solid product is then added to a mixture of the solvent, e.g. acetonitrile, and the the crown ether. Conveniently, 0.01–1.0 moles (preferably 0.05–0.25 moles) of the crown ether to 1 mole of original phenol are used. The resulting mixture is then stirred at room temperature for 30 minutes to allow the crown ether to act upon the sodium phenoxide.

Thereafter, N-(1-methyl)-3-phenyl-2-oxiranecarboxamide (V) (0.8–1.1 moles to 1 mole of initial phenol) is added to the stirred mixture, and this reaction mixture is then heated under reflux for 1 to 10 hours (5–7 hours preferred) to produce the α-hydroxy-β-phenoxy-N-(1-methylethyl)benzenepropanamide (VI).

An alternative and preferred method of preparing the alkali metal aryloxide reactant is begun by suspending the alkali metal hydride in the solvent, e.g. acetonitrile, and then adding the arylalcohol and the crown ether to this suspension. The presence of the crown ether at this stage enhances the solubility of the alkali metal aryloxide and the corresponding alkali metal cation and aryloxide anion in the solvent. This mixture is stirred at room temperature for 10 minutes to 2 hours before addition of the 3-phenyl-2-oxiranecarboxamide (V) reactant.

Those skilled in the art of chemistry will appreciate that other alkali metal cations may be used with the subject aryloxy anions (i.e. the anions whose aryl group is represented by X in Formula I). Sodium and potassium are the preferred alkali metal cations for this process, and the sodium cation is particularly preferred. Other metal cations and ammonium cations which will form salts with the aryloxy anion may also be utilized in the process of the invention. Such alkali metal aryloxide ion pair may be formed in situ as described with the use of sodium hydride, or such aryloxy alkali metal ion pair may be added directly as a reactant. Generally, it will be preferable to add the crown ether to the reactant mixture of the alkali metal aryloxide in the solvent prior to addition of the 3-phenyl-2-oxiranecarboxamide (V) reactant to aid in solvation of the anion-cation pair.

In carrying out the nucleophilic addition of an aryloxy group to the 3-position of a 3-phenyl-2-oxiranecarboxamide (V), aprotic organic solvents such as acetonitrile, benzene, dioxane, and acetone are preferred because of the solubility of the 3-phenyl-2-oxiranecarboxamide reactant and of the α-hydroxy-β-aryloxybenzenepropane product therein.

Numerous crown ethers are known which will form stable complexes with the alkali metal cation (or other metal cation) of a reactant alkali metal cation-nucleophilic anion salt. For a review of such crown ethers reported on in the chemical literature through December, 1972, see Christensen et al., Chem. Rev., 74, 351 (1974). With respect to the Applicants' process invention, however, the saturated (i.e. non-aromatic) and the simple (i.e. cyclic ether ring not substituted) crown ethers are preferred because of their greater solubility in the preferred organic solvents. For example, dicyclohexyl-18-crown-6 (saturated), 15-crown-5 (simple), and 18-crown-6 (simple) crown ethers are particularly preferred for the process of the invention. Another reason these crown ethers are preferred is that their "hole" size corresponds most closely to the size necessary to form the most stable complex with the preferred sodium cation. As described in Knipe, supra, at 619, and more fully in Thomassen et al., supra, and in Pedersen, J. Am. Chem. Soc., 89, 7017 (1967), the optimum crown ethers for forming a stable complex with a particular metal cation will generally be those crown ethers having a "hole" size sufficient to fully enclose one such ion within one molecule of the crown ether. Thus, with alkali metal cations other than the preferred sodium cation, the preferred crown ethers will vary in size according to the size of the particular cation. One skilled in the art will readily be able to determine appropriate crown ethers for use in the process of the invention.

The formation of a stable complex of the metal cation with the crown ether accounts for the improved solvation of the aryloxy anion in an aprotic organic solvent and for an enhanced nucleophilic reactivity of the aryloxy anion. However, these factors do not foretell the selectivity of the aryloxy anion for the 3-position of the 3-phenyl-2-oxiranecarboxamide in Applicants' process invention.

As used herein, the term "crown ether" describes macrocyclic ethers, including such ethers which are polycyclic and those in which sulfur or nitrogen atoms are substituted for one or more of the oxygen atoms in the cyclic ring. This scope of the term "crown ether" is coextensive with that described by Knipe, supra, at 618–19.

The preparation of crown ethers is described in Pedersen, supra; Knipe, supra; and Fieser and Fieser, Vol. 5, supra. The preparation of 18-crown-6 is described in Greene, Tetrahedron Letters, 1793 (1972) and in Gokel et al., J. Org. Chem., 39, 2445 (1974). Many crown ethers are available commercially.

E. In order to obtain the α-[(1-methylethylamine)methyl]-β-phenoxy-benzeneethanol (Ia) compound of the invention, the amide of the α-hydroxy-β-phenoxy-N-(1-methylethyl)benzenepropanamide (VI) is reduced to the corresponding amine. This reduction may be accomplished by the method of Brown and Heim, J. Org. Chem., 38, 912 (1973), in which an excess of borane-tetrahydrofuran complex (diborane in tetrahydrofuran) at 0° C. in a dry nitrogen atmosphere is brought into contact with a solution of α-hydroxy-β-phenoxy-N-(1-methylethyl)benzenepropanamide (VI) in tetrahydrofuran, keeping the temperature at 0° C. during the addition of the reactant. Thereafter, the solution is brought to reflux temperature and the reaction is run at reflux temperatures until completion. Separation of the reduction product is facilitated by the addition of dilute hydrochloric acid and further reflux heating of the reaction mixture.

For pharmacological use, the compounds of Formula I (Ia or Ib) may be administered in the form of an acid addition salt of a non-toxic organic or inorganic acid.

The salts may be prepared by methods well-known in the art. Such salts are included in the scope of the invention. Appropriate salts may be those formed from the following acids: hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic, benzenesulfonic, and oxalic.

The compounds of the invention exhibit anti-arrhythmic effects in warm-blooded animals as evidenced by standard pharmacologic tests in animals. The anti-arrhythmic activity of the compounds can be demonstrated by following a test procedure described by Baum et al., in Arch. Int. Pharmacodyn., 193, 149 (1971), which is a generally accepted test for anti-arrhythmic agents. In this test, the heart of an anesthetized (pentobarbital, 30–35 mg. I.V.) dog is exposed by a left thoracotomy. Bipolar electrodes are sutured to the epicardial surface of the left ventricle. The heart is stimulated with square wave pulses of 3 msec. duration and frequency of 60 Hz. for periods of 5 sec. Voltage is increased until fibrillation ensues. The heart is then defibrillated by DC countershock and the procedure repeated at 10 minute intervals. Drugs are administered intravenously over periods of 3 minutes and fibrillatory threshold examined 15 minutes after start of injection of each dose. Effective anti-arrhythmic agents elevate the fibrillatory threshold.

The compounds of the invention increase the fibrillatory threshold when administered according to this procedure at doses of 20 mg. per kilogram of body weight or less. Preferred compounds would exert only minimal depressant activity on systemic blood pressure.

When used to treat arrhythmia in warm-blooded animals, the effective dosage will depend upon the stage and severity of the condition being treated, the subject being treated, and the particular compound being used, and will readily be determined by the attending physician. Therapy should be initiated at lower dosages, usually 10 mg/kg. per day or less, the dosage thereafter being increased up to 20 mg/kg., if necessary, until the desired anti-arrhythmic effect is obtained.

The following examples further illustrate the best mode contemplated by the inventors for the practice of the invention.

EXAMPLE 1

4-Chlorocinnamoyl Chloride

Thionyl chloride (28.6 g.) was added dropwise to a benzene (300 ml.) solution of p-chlorocinnamic acid (36.5 g.) under stirring. The resulting solution was heated under reflux for 1 hour, then the solvent was evaporated under reduced pressure on a rotary evaporator to give the product, which melted at 78°–80° and weighed 40 g.

Analysis for: $C_9H_6Cl_2O$: Calculated: C, 53.76; H, 3.01. Found: C, 54.09; H, 2.75.

EXAMPLE 2

3-Methoxycinnamoyl Chloride

Thionyl chloride (38 g.) was added dropwise to a mixture of 3-methoxycinnamic acid (50 g.) and benzene (500 ml.), and the resulting mixture was heated under reflux for 1.5 hours, then evaporated under reduced pressure on a rotary evaporator to give an oil. The oil solidified on standing at room temperature, giving 59 g. of the product. Analytical sample (m.p. 43°–45°) was obtained by recrystallization from petroleum ether.

Analysis for: $C_{10}H_9ClO_2$: Calculated: C, 61.08; H, 4.61. Found: C, 60.93; H, 4.52.

EXAMPLE 3

N-(1-Methylethyl)Cinnamoylcarboxamide

To a stirring mixture of isopropylamine (66 g.) and benzene (500 ml.) was added dropwise cinnamoyl chloride (84 g.) dissolved in benzene (100 ml.) under stirring. The stirring was continued for 2 hours at room temperature, then heated under reflux for 45 minutes. The reaction mixture was allowed to set at room temperature overnight. The precipitate which deposited was collected on a filter and washed with benzene, then discarded. The filtrate and washings were combined and washed with water, then dried over magnesium sulfate. Removal of benzene by evaporation on a rotary evaporator under reduced pressure gave a solid residue which was then recrystallized from ether, giving 96.5 g. of product, 105°–107°.

Analysis for: $C_{12}H_{15}NO$: Calculated: C, 76.15; H, 7.99; N, 7.40. Found: C, 76.03; H, 8.28; N, 7.35.

EXAMPLE 4

N-(1-Methylethyl)-3-Chlorocinnamoylcarboxamide

A mixture of 3-chlorocinnamic acid (25 g.), thionyl chloride (19.4 g.) and benzene (300 ml.) was heated under reflux for 2 hours, then evaporated under reduced pressure on a rotary evaporator to give an oil. The oil was dissolved in benzene (50 ml.), and the benzene solution was added slowly to a mixture of isopropylamine (25 g.) and benzene (300 ml.). The resulting mixture was allowed to stir at room temperature for 2 hours, and heated under mild reflux for 1 hour. It was then allowed to set at room temperature overnight. The precipitate thus separated was collected on a filter, and washed with benzene. The combined filtrate and washings were washed with water, then dried over potassium carbonate. Removal of benzene under reduced pressure on a rotary evaporator gave an oil which solidified on standing. The product melted at 92°–94°, and weighed 28 g.

Analysis for: $C_{12}H_{14}ClNO$: Calculated: C, 64.43; H, 6.31; N, 6.26. Found: C, 64.10; H, 6.14; N, 6.24.

EXAMPLE 5

N-(1-Methylethyl)-4-Chlorocinnamoylcarboxamide

4-Chlorocinnamoyl chloride (40 g.) dissolved in benzene (70 ml) was added slowly to a mixture of isopropylamine (26 g.) and benzene (450 ml.) under gentle heating. During the addition the mixture was stirred with a mechanical stirrer. The resulting mixture was heated under reflux for 1 hour, then allowed to stand overnight at room temperature. The precipitate thus separated was collected on a filter, and washed with benzene, then with water. The product melted at 183°–185°, and weighed 48 g.

Analysis for: $C_{12}H_{14}ClNO$: Calculated: C, 64.43; H, 6.31; N, 6.26. Found: C, 64.35; H, 6.35; N, 6.31.

EXAMPLE 6

N-(1-Methylethyl)-3-Methoxycinnamoylcarboxamide

This compound was prepared from 3-methoxycinnamoyl chloride (59 g.), isopropylamine (36.5 g.) and benzene (500 ml.) as described in Example 5. The compound melted at 82°-84° and weighed 64.5 g.

Analysis for: $C_{13}H_{17}NO_2$: Calculated: C, 71.20; H, 7.82; N, 6.39. Found: C, 71.48; H, 7.58; N, 6.42.

EXAMPLE 7

N-(1-Methylethyl)-3-Phenyl-2-Oxiranecarboxamide (V)

A mixture of N-(1-methylethyl)cinnamoylcarboxamide (18 g.), m-chloroperbenzoic acid (23.6 g.), 4,4'-thiobis(6-tert-butyl-m-cresol) (0.3 g.) and ethylene dichloride (250 ml.) was heated under gentle reflux for 1 hour, then chilled in ice. A precipitate (m-chlorobenzoic acid) was separated by filtration and washed with ethylene dichloride. The filtrate and washings were combined, and evaporated under reduced pressure on a rotary evaporator to give an amber oil. The oil was dissolved in chloroform (300 ml.) and the chloroform solution was washed with 5% aqueous sodium bicarbonate solution twice, then with saline. The chloroform solution was dried over magnesium sulfate, then evaporated under reduced pressure in a rotary evaporator to give an oil. The oil solidified on standing. The solid mass was recrystallized from ether giving 8.4 g. of product, m.p. 114°-115°.

Analysis for: $C_{12}H_{15}NO_2$: Calculated: C, 70.22; H, 7.37; N, 6.82. Found: C, 70.23; H, 7.23; N, 6.82.

EXAMPLE 8

N-(1-Methylethyl)-3-(3-Chlorophenyl)-2-Oxiranecarboxamide

This compound was prepared from N-(1-methylethyl)-3-chlorocinnamoylcarboxamide (22.4 g.), m-chloroperbenzoic acid (23.6 g.), 4,4'-thiobis(6-tert-butyl-m-cresol) (0.3 g.), and ethylene dichloride as described in Example 7, and purified by recrystallization from ether. The compound melted at 131°-133°, and weighed 14.5 g.

Analysis for: $C_{12}H_{14}ClNO_2$: Calculated: C, 60.13; H, 5.88; N, 5.84. Found: C, 60.31; H, 5.87; N, 5.85.

EXAMPLE 9

N-(1-Methylethyl)-3-(4-Chlorophenyl)-2-Oxiranecarboxamide

This compound was prepared from N-(1-methylethyl)-4-chlorocinnamoylcarboxamide (18.3 g.), m-chloroperbenzoic acid (19.4 g.), 4,4'-thiobis(6-tert-butyl-m-cresol) (0.3 g.), and ethylene dichloride (250 ml.) as described in Example 7, and purified by recrystallization from ether. The compound melted at 139°-141°, and weighed 11.7 g. The analytical sample which was obtained by another recrystallization from ether melted at 143°-145°.

Analysis for: $C_{12}H_{14}ClNO_2$: Calculated: C, 60.13; H, 5.89; N, 5.84. Found: C, 60.33; H, 5.93; N, 5.93.

EXAMPLE 10

N-(1-Methylethyl)-3-(3-Methoxyphenyl)-2-Oxiranecarboxamide

This compound was prepared from N-(1-methylethyl)-3-methoxycinnamoylcarboxamide (43.9 g.), m-chloroperbenzoic acid (46 g.), 4,4'-thiobis(6-tert-butyl-m-cresol) (0.6 g.), and ethylene dichloride (500 ml.) as described in Example 7. The compound obtained as an oil was used directly in the subsequent reaction.

EXAMPLE 11

α-Hydroxy-β-Phenoxy-N-(1-Methylethyl)Benzenepropanamide (VI)

Phenol (3.0 g.) was converted into its sodium salt by dissolving in a freshly prepared sodium methoxide-methanol solution (0.7 g. of metallic sodium in 50 ml. of absolute methanol), and subsequent evaporation of the excess methanol under reduced pressure on a rotary evaporator. The solid residue was dissolved in acetonitrile (250 ml.) by stirring with 18-crown-6 (0.9 g.) for 30 minutes at room temperature. N-(1-methylethyl)-3-phenyl-2-oxiranecarboxamide (6.16 g.) was added to the solution, and the resulting mixture was heated under reflux for 6 hours. After cooling to room temperature, it was filtered. The filtrate was evaporated on a rotary evaporator under reduced pressure to give a resinous material. Water (ca. 200 ml.) was added to the residue, and allowed to stand at room temperature. The white precipitate thus separated was collected on a filter and washed with water. The filter residue was dried in air, then recrystallized from ethanol, giving 2.5 g. of product, m.p. 166°-168°.

Analysis for: $C_{18}H_{21}NO_3$: Calculated: C, 72.21; H, 7.07; N, 4.68. Found: C, 71.86; H, 6.95; N, 4.67.

EXAMPLE 12

α-Hydroxy-62-(4-Methoxyphenoxy)-N-(1-Methylethyl)Benzenepropanamide

Sodium hydride (50% oil dispersion, 2.4 g.) was washed with pentane, then suspended in acetonitrile (500 ml.). 4-Methoxyphenol (6.2 g.) and 18-crown-6 (1.5 g.) was added to the suspension, and the resulting mixture was stirred at room temperature for 0.5 hours. To the mixture was added N-(1-methylethyl)-3-phenyl-3-oxiranecarboxamide (10.3 g.) and heated under reflux for 6 hours. The reaction mixture was filtered, and the filtrate was evaporated under reduced pressure on a rotary evaporator to give an oil. Treatment of the oil with water (ca. 300 ml.) caused separation of a white precipitate which was collected on a filter, and washed with water. The filter residue was dried, then recrystallized from ether, giving 4.6 g. of product, m.p. 134°-136°.

Analysis for: $C_{19}H_{23}NO_4$: Calculated: C, 69.23; H, 7.04; N, 4.25. Found: C, 69.23; H, 6.96; N, 4.25.

EXAMPLE 13

α-Hydroxy-β-(3-Methoxyphenoxy)-N-(1-Methylethyl)Benzenepropanamide

This compound was prepared from N-(1-methylethyl)-3-phenyl-2-oxiranecarboxamide (10.3 g.), m-methoxyphenol (6.2 g.), sodium hydride (50% oil dispersion, 2.4 g.), 18-crown-6 (1.5 g.) and acetonitrile (500 ml.) as described in Example 12. The crude product (m.p. 118°-120°, yield 2.6 g.) was then recrystallized from ether with a small amount of tetrahydrofuran, giving 2.3 g. of the pure product, m.p. 132°-133°.

Analysis for: $C_{19}H_{23}NO_4$: Calculated: C, 69.28; H, 7.04; N, 4.25. Found: C, 68.99; H, 7.00; N, 4.21.

EXAMPLE 14

α-Hydroxy-β-(4-Methylphenoxy)-N-(1-Methylethyl)-Benzenepropanamide

This compound was prepared as in Example 12 from N-(1-methylethyl)-3-phenyl-2-oxiranecarboxamide (6.16 g.), p-cresol (3.3 g.), sodium hydride (50% oil dispersion, 1.5 g.), 18-crown-6 (0.9 g.) and acetonitrile (250 ml.). The product melted at 152°–152°, and amounted to 2.4 g.

Analysis for: $C_{19}H_{23}NO_3$: Calculated: C, 72.82; H, 7.40; N, 4.47. Found: C, 72.89; H, 7.42; N, 4.49.

EXAMPLE 15

α-Hydroxy-β-(3-Methylphenoxy)-N-(1-Methylethyl)-Benzenepropanamide

This compound was prepared as in Example 12 from N-(1-methylethyl)-3-phenyl-2-oxiranecarboxamide (6.16 g.), m-cresol (3.3 g.), sodium hydride (50% oil dispersion, 1.5 g.), 18-crown-6 (0.9 g.), and acetonitrile (250 ml.). The product which was recrystallized from ether melted at 158°–159°, and weighed 3.2 g.

Analysis for: $C_{19}H_{23}NO_3$: Calculated: C, 72.82; H, 7.40; N, 4.47. Found: C, 72.57; H, 7.36; N, 4.42.

EXAMPLE 16

α-Hydroxy-β-(2-Methylphenoxy)-N-(1-Methylethyl)-Benzenepropanamide

This compound was prepared from N-(1-methylethyl)-3-phenyl-2-oxiranecarboxamide (8.2 g.) o-cresol (4.3 g.), sodium hydride (50% oil dispersion, 1.9 g.), 18-crown-6 (1.0 g.), and acetonitrile (250 ml.) as described in Example 12. The compound after recrystallization from ether melted at 123°–124°, and weighed 1.25 g.

Analysis for: $C_{19}H_{23}NO_3$: Calculated: C, 72.82; H, 7.40; N, 4.47. Found: C, 72.79; H, 7.24; N, 4.48.

EXAMPLE 17

α-Hydroxy-β-(4-Chlorophenoxy)-N-(1-Methylethyl)-Benzenepropanamide

This compound was prepared from N-(1-methylethyl)-3-phenyl-2-oxiranecarboxamide (6.16 g.) p-chlorophenol (3.9 g.), sodium hydride (50% oil dispersion, 1.5 g.) 18-crown-6 (0.9 g.), and acetonitrile (250 ml.) as described in Example 12. The product melted at 148°–150°, and amounted to 2.7 g.

Analysis for: $C_{18}H_{20}ClNO_3$: Calculated: C, 64.76; H, 6.04; N, 4.20. Found: C, 64.34; H, 5.81; N, 4.27.

EXAMPLE 18

α-Hydroxy-β-(3-Chlorophenoxy)-N-(1-Methylethyl)-Benzenepropanamide

This compound was prepared from N-(1-methylethyl)-3-phenyl-2-oxiranecarboxamide (6.16 g.) m-chlorophenol (3.9 g.), sodium hydride (50% oil dispersion, 1.5 g.), 18-crown-6 (0.9 g.), and acetonitrile (250 ml.) as described in Example 12. The product which was purified by recrystallization from ether melted at 151°–153°, and weighed 1.4 g.

Analysis for: $C_{18}H_{20}ClNO_3$: Calculated: C, 64.76; H, 6.04; N, 4.20. Found: C, 64.41; H, 6.22; N, 4.30.

EXAMPLE 19

α-Hydroxy-β-(1-Naphthoxy)-N-(1-Methylethyl)Benzenepropanamide.¼ EtOAc

This compound was prepared from N-(1-methylethyl)-3-phenyl-2-oxiranecarboxamide (8.2 g.), 1-naphthol (5.8 g.), sodium hydrode (50% oil dispersion, 1.9 g.) and acetonitrile (250 ml.) as described in Example 12, except that the mixture of 1-naphthol, sodium hydride, 18-crown-6 and acetonitrile was allowed to stir at room temperature for 1 hour. The crude product was recrystallized from a small amount of ethyl acetate, giving 3.0 g. of the product which contained a ¼ mole of ethyl acetate per mole of α-hydroxy-β-(1-naphthoxy)-N-(1-methylethyl)benzenepropanamide, m.p. 183°–185°.

Analysis for: $C_{22}H_{23}NO_3.\frac{1}{4}$ EtOAc: Calculated: C, 74.37; H, 6.78; N, 3.77. Found: C, 74.14; H, 6.36; N, 3.88.

EXAMPLE 20

α-Hydroxy-β-Phenoxy-N-(1-Methylethyl)-3-Chlorobenzenepropanamide

This compound was prepared from N-(1-methylethyl)-3-(3-chlorophenyl)-2-oxiranecarboxamide (7.2 g.), phenol (3.0 g.), sodium hydride (50% oil dispersion, 1.6 g.), 18-crown-6 (0.9 g.) and acetonitrile (250 ml.) as described in Example 12. The crude product was recrystallized from ether. The compound melted at 160°–162°, and weighed 1.7 g.

Analysis for: $C_{18}H_{20}ClNO_3$: Calculated: C, 64.76; H, 6.04; N, 4.20. Found: C, 64.52; H, 6.04; N, 4.18.

EXAMPLE 21

α-Hydroxy-β-Phenoxy-N-(1-Methylethyl)-4-Chlorobenzenepropanamide

This compound was prepared from N-(1-methylethyl)-3-(4-chlorophenyl)-2-oxiranecarboxamide (7.2 g.), phenol (3.0 g.), sodium hydride (50% oil dispersion, 1.6 g.), 18-crown-6 (0.9 g.), and acetonitrile (250 ml.) as described in Example 12. The crude product was recrystallized from ethanol, giving 2.3 g. of the compound, m.p. 175°–177°. Another recrystallization from ethanol gave analytical sample, m.p. 176°–178°.

Analysis for: $C_{18}H_{20}ClNO_3$: Calculated: C, 64.76; H, 6.04; N, 4.20. Found: C, 64.44; H, 6.21; N, 4.08.

EXAMPLE 22

α-Hydroxy-β-Phenoxy-N-(1-Methylethyl)-3-Methoxybenzenepropanamide

This compound was prepared from N-(1-methylethyl)-3-(3-methoxyphenyl)-2-oxiranecarboxamide (14.3 g.), phenol (6.0 g.), sodium hydride (50% oil dispersion, 3.2 g.), 18-crown-6 (1.8 g.), and acetonitrile (500 ml.) as described in Example 12. The compound obtained as an oil was used directly in the subsequent reaction.

EXAMPLE 23

α-Hydroxy-β-(4-Chlorophenoxy)-N-(1-Methylethyl)-4-Chlorobenzenepropanamide

This compound was prepared from N-(1-methylethyl)-3-(4-chlorophenyl)-2-oxiranecarboxamide (9.56 g.), p-chlorophenol (5.2 g.), sodium hydride (50% oil dispersion, 2.0 g.) 18-crown-6 (3.0 g.), and acetonitrile (300 ml.) as described in Example 12, and purified by recrystallization from ether. The compound melted at 177°–179°, and weighed 0.76 g.

Analysis for: $C_{18}H_{19}Cl_2NO_3$: Calculated: C, 58.71; H, 5.20; N, 3.80. Found: C, 58.80; H, 5.24; N, 3.91.

EXAMPLE 24

α-[(1-Methylethylamino)methyl]-β-Phenoxy-Benzeneethanol (Ia)

Borane-tetrahydrofuran complex (1 M solution in tetrahydrofuran, 20 ml.) was transferred by a syringe to a 100 ml. three-neck flask equipped with a reflux condenser, a nitrogen gas inlet and a rubber septum. The reaction flask was then chilled in a mixture of ice and table salt. α-Hydroxy-β-phenoxy-N-(1-methylethyl)-benzenepropanamide (1.9 g.) suspended in tetrahydrofuran (25 ml.) was added slowly keeping the temperature at ca. 0°. The solution thus obtained was brought to reflux and maintained there for 2.5 hours. The reaction mixture was cooled to room temperature, dilute hydrochloric acid (6 N HCl 3 ml.) and water (5 ml.) was added carefully, and the mixture was heated under reflux for 20 minutes. It was then evaporated on a rotary evaporator under reduced pressure to give a solid residue. The residue was treated with water. The water insoluble material was separated by collecting on a filter and washed with water. The filtrate and washings were combined and made alkaline by addition of 50% aqueous sodium hydroxide solution, then extracted with chloroform 3 times. The combined extract was dried over magnesium sulfate, and evaporated under reduced pressure to give an oil which solidified on standing. The crude product was recrystallized from ether and petroleum ether, giving 1.0 g. of product, m.p. 95°–96°.

Analysis for: $C_{18}H_{23}NO_2$: Calculated: C, 75.75; H, 8.12; N, 4.91. Found: C, 75.92; H, 8.26; N, 4.92.

EXAMPLE 25

α-[(1-Methylethylamino)methyl]-β-(4-Methoxyphenoxy)Benzeneethanol, Nitrate

α-Hydroxy-β-(4-methoxyphenoxy)-N-(1-methylethyl)benzenepropanamide, (3.3 g.) was reduced with borane-tetrahydrofuran complex (1 M solution in tetrahydrofuran, 25 ml.) as described in Example 24 and treated with dilute hydrochloric acid (6 N, HCl, 5 ml.). The reduction product (3.7 g.) was obtained as an oil which failed to solidify. The oily product was dissolved in absolute ethanol, and filtered. Concentrated nitric acid (1.05 g.) was added with caution to the chilled filtrate. The resulting mixture was diluted with anhydrous ether (ca. 100 ml.), and chilled in ice. The precipitate thus separated was collected on a filter and washed with ethanol, giving 2.9 g. of product, m.p. 153°–155°.

Analysis for: $C_{19}H_{25}NO_3.HNO_3$: Calculated: C, 60.30; H, 6.93; N, 7.40. Found: C, 60.10; H, 7.09; N, 7.53.

EXAMPLE 26

α-[(1-Methylethylamino)methyl]-β-(3-Methoxyphenoxy)Benzeneethanol, Nitrate

This compound was prepared by reduction of α-hydroxy-β-(3-methoxyphenoxy)-N-(1-methylethyl)-benzenepropanamide (2.2 g.) with borane-tetrahydrofuran complex (1 M solution in tetrahydrofuran, 16.6 ml.) as described in Example 24. The product which was obtained as an oil was converted into its nitric acid salt, and recrystallized from a small amount of ethanol and ether. The product melted at 107°–109°, and weighed 0.6 g.

Analysis for: $C_{19}H_{25}NO_3.HNO_3$: Calculated: C, 60.30; H, 6.93; N, 7.40. Found: C, 60.54; H, 6.93; N, 7.71.

EXAMPLE 27

α-[(1-Methylethylamino)methyl]-β-(4-Methylphenoxy)Benzeneethanol, Nitrate

This compound was prepared by reduction of α-hydroxy-β-(4-methylphenoxy)-N-(1-methylethyl)benzenepropanamide (1.6 g.) with borane-tetrahydrofuran complex (1 M solution in tetrahydrofuran, 13 ml.) as described in Example 24. The product was obtained as an oil which was converted into the nitrate salt in the following fashion: The oil was dissolved in a small amount of absolute ethanol, and the ethanol solution was made acidic by addition of concentrated nitric acid. Since addition of anhydrous ether and chilling in ice failed to cause separation by a precipitate, it was evaporated under reduced pressure on a rotary evaporator to give a resinous material. Addition of anhydrous ether to the residue gave a solid residue which melted at 138°–140°, and weighed 1.3 g.

Analysis for: $C_{19}H_{25}NO_2.HNO_3$: Calculated: C, 62.96; H, 7.23; N, 7.73. Found: C, 62.72; H, 7.30; N, 7.79.

EXAMPLE 28

α-[(1-Methylethylamino)methyl]-β-(3-Methylphenoxy)Benzeneethanol, Nitrate

This compound was prepared as in Example 24 from α-hydroxy-β-(3-methylphenoxy)-N-(1-methylethyl)-benzenepropanamide (1.6 g.) and borane-tetrahydrofuran complex (1 M solution in tetrahydrofuran, 13 ml.). The oily product was then converted into nitric acid salt, m.p. 127°–129°, yield 0.8 g.

Analysis for: $C_{19}H_{25}NO_2.HNO_3$: Calculated: C, 62.96; H, 7.23; N, 7.73. Found: C, 62.70; H, 7.37; N, 7.61.

EXAMPLE 29

α-[(1-Methylethylamino)methyl]-β-(2-Methylphenoxy)Benzeneethanol, Hydrochloride

This compound was prepared by reduction of α-hydroxy-N-(1-methylethyl)-β-(2-methylphenoxy)benzenepropanamide (1.8 g.) with borane-tetrahydrofuran complex (1 M solution in tetrahydrofuran, 13 ml.) and subsequent treatment with hydrochloric acid as described in Example 24. The crude product was purified by recrystallization from tetrahydrofuran. The product melted at 193°–195°, and weighed 0.75 g.

Analysis for: $C_{19}H_{25}NO_2.HCl$: Calculated: C, 67.94; H, 7.80; N, 4.17. Found: C, 67.64; H, 7.65; N, 4.26.

EXAMPLE 30

α-[(1-Methylethylamino)methyl]-β-(4-Chlorophenoxy)Benzeneethanol, Nitrate

This compound was prepared as in Example 25 by reduction of β-(3-chlorophenoxy)-α-Hydroxy-N-(1-methylethyl)benzenepropanamide (1.4 g.) with borane-tetrahydrofuran complex (1 M solution in tetrahydrofuran, 10 ml.) and following salt formation with nitric acid. The product melted at 157°–159°, and weighed 0.55 g.

Analysis for: $C_{18}H_{22}ClNO_2.HNO_3$: Calculated: C, 56.46; H, 6.05; N, 7.32. Found: C, 56.39; H, 6.11; N, 7.20.

EXAMPLE 31

α-[(1-Methylethylamino)methyl]-β-(3-Chlorophenoxy)Benzeneethanol, Nitrate

This compound was obtained by reduction of α-hydroxy-β-(3-chlorophenoxy)-N-(1-methylethyl)-benzenepropanamide (1.6 g.) with borane-tetrahydrofuran complex (1 M solution in tetrahydrofuran, 12 ml.) and subsequent treatment of the oily product with nitric acid as described in Example 25. The product melted at 112°–114°, and weighed 0.55 g.

Analysis for: $C_{18}H_{22}ClNO_2.HNO_3$: Calculated: C, 56.46; H, 6.05; N, 7.32. Found: C, 56.44; H, 5.76; N, 7.19.

EXAMPLE 32

α-[(1-Methylethylamino)methyl]-β-(1-Naphthoxy)Benzeneethanol, Nitrate

This compound was prepared by reduction of α-hydroxy-β-(1-naphthoxy)-N-(1-methylethyl)benzenepropanamide (3.5 g.) with borane-tetrahydrofuran (1 M solution in tetrahydrofuran, 25 ml.) and subsequent treatment of the oily product with nitric acid as described in Example 25. The product melted at 157°–159°, weighed 1.25 g.

Analysis for: $C_{22}H_{25}NO_2.HNO_3$: Calculated: C, 66.31; H, 6.58; N, 7.03. Found: C, 65.93; H, 6.61; N, 7.02.

EXAMPLE 33

α-[(1-Methylethylamino)methyl]-β-Phenoxy-3-Chlorobenzeneethanol, Nitrate

This compound was prepared by reduction of α-hydroxy-β-phenoxy-N-(1-methylethyl)-(3-chlorobenzene)propanamide (1.6 g.) with borane-tetrahydrofuran complex (1 M solution in tetrahydrofuran, 12 ml.) and converting the oily product into nitric acid salt, as described in Example 25. The compound melted at 95°–97°, and weighed 1.05 g.

Analysis for: $C_{18}H_{22}ClNO_2.HNO_3$: Calculated: C, 56.46; H, 6.05; N, 7.32. Found: C, 56.34; H, 6.26; N, 7.13.

EXAMPLE 34

α-[(1-Methylethylamino)methyl]-β-Phenoxy-3-Methoxybenzeneethanol, ½ Oxalate, ¼ Hydrate This compound was prepared by reduction of α-hydroxy-β-phenoxy-N-(1-methylethyl)-3-methoxybenzenepropanamide and borane-tetrahydrofuran complex (1 M solution in tetrahydrofuran), and the oily product was converted into oxalic acid salt. The compound which was obtained as ½ oxalate, ¼ hydrate melted at 187°–190° dec.

Analysis for: $C_{19}H_{25}NO_3.\tfrac{1}{2}$ $(CO_2H_2.\tfrac{1}{4}$ $H_2O$: Calculated: C, 65.83; H, 7.32; N, 3.84. Found: C, 65.80; H, 7.31; N, 4.10.

What is claimed is:

1. A process which comprises reacting a 3-phenyl-2-oxiranecarboxamide of the formula:

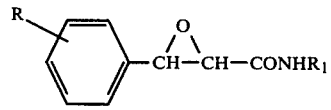

wherein R is hydrogen, halogen, lower alkyl or lower alkoxy and $R_1$ is lower alkyl, with an alkali metal aryloxide in the presence of a crown ether to yield a 3-aryloxy-3-phenyl-1-alkylamino-2-propanol of the formula:

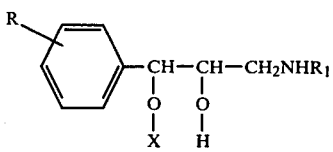

wherein R and $R_1$ are as defined above and X is phenyl, 1-naphthyl, or a phenyl group substituted by a halogen, a lower alkyl group, or a lower alkoxy group, in which the aryloxide anion has the formula XO, where X is as defined above.

2. A process according to claim 1 wherein said alkali metal is sodium and said crown ether is 18-crown-6.

3. A process according to claim 1 wherein said alkali metal is sodium and said crown ether is dicyclohexyl-18-crown-6.

4. A process according to claim 1 wherein said alkali metal is sodium and said crown ether is 15-crown-5.

5. A process according to claim 1 wherein the alkali metal is sodium or potassium.

* * * * *